United States Patent
Strange et al.

(10) Patent No.: US 11,638,544 B2
(45) Date of Patent: May 2, 2023

(54) POROUS OPTICAL FIBER FOR THE DETECTION OF AN ANALYTE IN A FLUID

(71) Applicant: Radiometer Medical ApS, Brønshøj (DK)

(72) Inventors: Christian Strange, Brønshøj (DK); Thomas Kjaer, Brønshøj (DK)

(73) Assignee: RADIOMETER MEDICAL APS, Brønshøj (DK)

( * ) Notice: Subject to any disclaimer, the term of this patent is extended or adjusted under 35 U.S.C. 154(b) by 625 days.

(21) Appl. No.: 16/613,466

(22) PCT Filed: May 15, 2018

(86) PCT No.: PCT/EP2018/062441
§ 371 (c)(1),
(2) Date: Nov. 14, 2019

(87) PCT Pub. No.: WO2018/210784
PCT Pub. Date: Nov. 22, 2018

(65) Prior Publication Data
US 2021/0153782 A1    May 27, 2021

(30) Foreign Application Priority Data
May 17, 2017 (DK) .......................... PA 2017 70345

(51) Int. Cl.
*A61B 5/1455* (2006.01)
*A61B 5/145* (2006.01)
(Continued)

(52) U.S. Cl.
CPC ........ *A61B 5/1455* (2013.01); *A61B 5/14546* (2013.01); *G01N 15/1434* (2013.01);
(Continued)

(58) Field of Classification Search
CPC .............. A61B 5/14546; A61B 5/1455; G01N 15/1434; G01N 2015/0065; G01N 21/62;
(Continued)

(56) References Cited

U.S. PATENT DOCUMENTS

| | | |
|---|---|---|
| 4,975,581 A | 12/1990 | Robinson et al. |
| 5,250,095 A | 10/1993 | Sigel, Jr. et al. |

(Continued)

FOREIGN PATENT DOCUMENTS

| | | |
|---|---|---|
| CA | 2 270 276 A1 | 10/2000 |
| JP | S 56100046 A | 8/1981 |

(Continued)

OTHER PUBLICATIONS

Indian Patent Certificate of Indian Patent No. 382974 (one page).
(Continued)

*Primary Examiner* — Tri T Ton
(74) *Attorney, Agent, or Firm* — Finnegan, Henderson, Farabow, Garrett & Dunner LLP (57) ABSTRACT

The invention relates to a porous optical fiber for the detection of an analyte in a fluid by optical probing. The optical fiber has a first end and a second end opposite to the first end, as seen in a longitudinal direction, and a circumferential surface delimiting the optical fiber in radial directions perpendicular to the longitudinal direction. The optical fiber comprises a core adapted for supporting at least one optical mode propagating in the longitudinal direction, the core having a circumferential interface delimiting the core in the radial directions. The optical fiber further comprises pores penetrating from an opening at the circumferential surface through the circumferential interface into the core of the optical fiber, wherein a cross-sectional dimension of the openings is dimensioned so as to prevent a particulate
(Continued)

fraction of the fluid from entering the pores, while allowing the analyte to enter the pores.

21 Claims, 3 Drawing Sheets

(51) Int. Cl.
| | | |
|---|---|---|
| | *G01N 15/14* | (2006.01) |
| | *G01N 21/62* | (2006.01) |
| | *G01N 33/49* | (2006.01) |
| | G01N 21/77 | (2006.01) |
| | G01N 15/00 | (2006.01) |

(52) U.S. Cl.
CPC ............. *G01N 21/62* (2013.01); *G01N 33/49* (2013.01); *G01N 21/7703* (2013.01); *G01N 2015/0065* (2013.01)

(58) Field of Classification Search
CPC ................ G01N 21/7703; G01N 33/49; B65B 2220/16; B65B 25/008; B65B 43/185; B65B 43/265; B65B 43/325; B65B 43/52; B65B 5/024; B65B 5/10; B65B 51/02; B65B 57/02; B65B 59/003; B65B 59/005; G06N 20/00; G06Q 10/04; G06Q 10/0832; G06Q 10/087
USPC ...... 600/309; 356/335–343, 432–444, 243.2, 356/73.1, 460, 465, 477, 901
See application file for complete search history.

(56) References Cited

U.S. PATENT DOCUMENTS

| | | | |
|---|---|---|---|
| 5,953,477 | A | 9/1999 | Wach et al. |
| 2002/0163639 | A1* | 11/2002 | Stephenson ............... G01J 3/44 356/301 |
| 2002/0176675 | A1* | 11/2002 | Oyamada .......... C03B 37/01225 356/73.1 |
| 2004/0264901 | A1* | 12/2004 | Tao ..................... G01N 21/7703 385/12 |
| 2010/0166359 | A1 | 7/2010 | Fujimaki et al. |
| 2010/0182607 | A1* | 7/2010 | Chau .................. G01N 21/7703 385/12 |
| 2011/0091515 | A1* | 4/2011 | Zilberman ............ A61L 15/425 424/443 |
| 2017/0031091 | A1* | 2/2017 | Yin ................... C04B 35/62236 |
| 2017/0059469 | A1* | 3/2017 | Hutter ................ G01N 15/1434 |

FOREIGN PATENT DOCUMENTS

| | | |
|---|---|---|
| JP | 3-114441 | 5/1991 |
| JP | 11-508475 | 7/1999 |
| JP | 2003-149215 | 5/2003 |
| WO | WO 97/26033 | 7/1997 |
| WO | WO 2004/090510 A1 | 10/2004 |

OTHER PUBLICATIONS

Intimation of Grant and Recordal of Patent No. 382974 (one page).
Tao, Shiquan et al., "Optical-Fiber Sensor Using Tailored Porous Sol-Gel Fiber Core," IEEE Sensors Journal, vol. 4, No. 3, pp. 322-328 (2004).
Ho, Wing Fat et al., "Porous Polyethylene Terephthalate Optical Waveguide for Sensing Applications," IEEE Photonics Technology Letters, vol. 25, No. 17, pp. 1672-1675 (2013).
International Search Report for International Application No. PCT/EP2018/062441, dated Aug. 8, 2018 (three pages).
Written Opinion of the International Searching Authority for International Application No. PCT/EP2018/062441 (five pages).

* cited by examiner

POROUS OPTICAL FIBER FOR THE DETECTION OF AN ANALYTE IN A FLUID

This application is a national stage filing under 35 U.S.C. § 371 of International Application No. PCT/EP2018/062441, filed on May 15, 2018, which claims priority of Danish Patent Application No. PA 2017 70345, filed on May 17, 2017. The contents of these applications are each incorporated herein by reference.

The present invention relates in one aspect to a porous optical fiber for the detection of an analyte in a fluid by optical probing. In a further aspect, the invention relates to a system for the detection of an analyte in a fluid comprising a porous optical fiber. In a particular aspect, the fluid is a body fluid, such as whole blood. In a further particular aspect, the porous optical fiber and the system comprising the porous optical fiber are for the detection of hemolysis, in particular in a whole blood sample.

BACKGROUND OF THE INVENTION

Detecting an analyte in a complex fluid containing continuous and discontinuous fractions is a challenging, but frequently encountered measurement problem. Typically the measurements involve steps of sample preparation including separation, e.g. by filtration, sedimentation and/or centrifugation, and subsequent detection measurement steps using chemical indication reactions and/or physical interactions sensitive to the analyte in question. An intricate challenge in this context is often the preparation and presentation of a proper sample for the detection without compromising the measurement, in particular if a volume of the available sample is small, and if the fluid to be analyzed is very complex. On top of that, very often in such a situation, multiple parameters are to be determined on the same sample, which imposes additional constraints of integrating a given measurement for the detection of an analyte with measurements of other parameters.

Therefore there is a need for a highly sensitive, yet simple and fast technique allowing for the selective detection of an analyte in a complex fluid, which is furthermore adapted for easy integration with other measurement techniques for determining multiple parameters of the same sample. The desired technique is furthermore required to provide for gentle separation, extraction, and/or isolation of the analyte for the detection measurements, i.e. without compromising the remaining fractions of the fluid to be analyzed.

Such a detection technique is relevant for various industries, ranging from food industry, over waste water treatment, to pharmaceutical applications and medical devices, where known techniques often require large sample volumes and time consuming analysis procedures.

One example for the application of such a measurement technique is in relation to the detection of an analyte in a patient's blood sample. The analyte can be any of a laboratory's test parameters for blood analysis which is detectable by light, e.g. spectrophotometry. As one source of interference, hemolysis may affect the measurement of a number of blood parameters as determined in blood parameter analyzers. Disregarding a level of free hemoglobin in the blood sample may thus mislead an unaware person and as a result provide a wrong diagnosis based on the affected blood parameter value. However, reliably determining a level of free hemoglobin present in the plasma fraction of a whole blood sample hitherto involved a complex process requiring separation of the plasma fraction from the cellular components and a subsequent analysis of the separated plasma fraction. Such a procedure is time consuming and may be prohibitive in cases where only very small samples are available at a time, such as in neonatal care with a continued monitoring of blood parameters in the infant. Other approaches for measuring components present in the plasma fraction in whole blood involve the separation of a plasma fraction from cellular components by microfiltration techniques in e.g. a microfluidic device, prior to analysis of the plasma fraction in a dedicated measurement in the microfluidic device. For example, a recent scientific article by Archibong et al. and published in Sensing and Bio-Sensing Research 3 (2015), p. 1-6, discloses a miniature measuring chamber for optically analyzing a plasma fraction that has been separated from a whole blood sample. In this type of device, a miniature microfluidic chamber is attached to the interface of an optical fiber. The bottom of the microfluidic chamber consists of a porous membrane that allows fluids and chemical compounds to flow inside the device, while at the same time filtering out undesired particles. The inside of the microfluidic chamber receiving the filtrate can be optically probed through a single optical fiber in normal-incidence reflection geometry.

In a further example, namely applications in food industries, such as a dairy industry, most traditional methods of filtering and detecting comprise filter paper, sieves and the like for visual inspection, spectrometry or bacterial counting of the residues with the above-mentioned disadvantages of requiring relatively large sample volumes and involving time-consuming measuring procedures that are detrimental to the sample, and that are incompatible with integrated multiple-parameter measurements to be performed on the same sample. Similar challenges are also encountered in the field of environmental technologies, such as waste water analysis and treatment, where most traditional methods of filtering and detecting comprise filter papers, sieves and the like for spectrometry and bacterial counting of the residues.

However, such filtration-based approaches have several disadvantages when used for analyzing e.g. whole blood samples. Filtration devices inherently rely on a fluid flow of at least the filtrate through the pores of the filter from a sample feed to a filtrate analysis/measurement chamber. In through-flow geometries, the retentate (here the red blood cells) gradually clogs the filtration pores. In crossflow geometries, the retentate is lead along the surface of the filtering membrane, thereby reducing but not removing the problem with clogging, especially if the system is intended for repetitive use (more than 10-100 samples). Crossflow geometry also induces friction and shear interaction between the retentate and the surface of the filtering device. The disclosed device is most useful as a disposable rather than for continued and repetitive use, since a complete washout of a sample after measurement may be difficult or at least very time-consuming and unreliable, at the further risk of cross-contamination between subsequent samples. In this particular type of device, additional challenges for obtaining quantitative results from the optical probing may arise, due to pressure-induced deformation of the filtration membrane resulting in a change of the optical path for probing the filtrate.

Therefore, there is a need for an improved device and method for the detection of an analyte in a fluid with a fast and reliable response, and which facilitates easy integration. More generally, there is a need for an improved device and method for the detection of substances in a fraction of a complex fluid, such as a whole blood sample with a fast and reliable response, which is adapted for integration in a fluid analyzer system, in particular an analyzer system for multiple-parameter measurements on the same fluid sample.

Object of the present invention is to provide an improved detection overcoming at least some of the disadvantages of known devices, sensors, systems and/or methods for specific detection of analytes in the continuous fraction of a complex fluid, such as for detecting an analyte in a plasma fraction of a whole blood sample.

SUMMARY OF THE INVENTION

The object of the invention is achieved by the porous fiber and sensor system as defined in the attached claims as well as by embodiments thereof as further detailed below.

A first aspect of the invention relates to a porous optical fiber for the detection of an analyte in a fluid by optical probing; the optical fiber having a first end and a second end opposite to the first end, as seen in a longitudinal direction, and a circumferential surface delimiting the optical fiber in radial directions perpendicular to the longitudinal direction; the optical fiber comprising: a core adapted for supporting at least one optical mode propagating in the longitudinal direction, the core having a circumferential interface delimiting the core in the radial directions; and pores penetrating from an opening at the circumferential surface through the circumferential interface into the core of the optical fiber, wherein a cross-sectional dimension of the openings is dimensioned so as to prevent a particulate fraction of the fluid from entering the pores, while allowing the analyte to enter the pores.

The circumferential surface of the porous optical fiber is for contacting a fluid to be analyzed. In an active region, the optical fiber is provided with small pores. Each of the small pores has an opening through which it can communicate with a fluid space outwardly adjacent to the circumferential surface with the openings. The pores thus allow for fluid communication between the depth of the pores located in the core of the optical fiber and the fluid space outwardly adjacent to the circumferential surface of the optical fiber. The pores extend from the respective opening at the circumferential surface into the core. The pores are formed integrally in the optical fiber with openings at the circumferential surface, in fluid communication with the fluid to be analyzed. Besides the core, the optical fiber may further comprise one or more layers surrounding the core, such as cladding or reflector layers adapted for confining light propagating along the optical fiber to the core. The core is delimited from such outer layers by a circumferential interface. Importantly, the pores penetrate from the circumferential surface of the optical fiber through the outer layers, if any, and further inward beyond the circumferential interface into the core of the optical fiber. Pore penetration into the core is determined as the depth of penetration of the pores from the circumferential interface defining the radial bounds of the core, and inwardly into the core material.

The openings of the pores are dimensioned such that a particulate fraction of the fluid to be analyzed is kept outside the pores, while allowing an analyte from a further fraction, e.g. a continuous fraction, to enter through the pores into the core of the optical fiber where an optical mode propagated through the core can interact with the analyte and thus detect the analyte by optical probing.

The porous optical fiber needs a light source and a detector arranged to optically probe the content of the pores, and to generate a corresponding signal output representative of the analyte content in a fluid. The probing optical field is typically injected into the core from one end, e.g. the first end, of the optical fiber, and the optical response is collected by a detector, which is arranged to receive output light emitted from the pores in response to illumination by the injected input light as further detailed below.

The pores form vials/cuvettes for selectively receiving an analyte from a first fraction of the fluid, in particular via diffusion/diffusive transport, whereas a particulate fraction is effectively prevented from entering the pores. These vials/cuvettes are placed in the core, i.e. in the path of the light propagating along the core, for efficient interaction of probing light with the analyte. By using an optical fiber, the probing light is easily coupled into and delivered to a sensitive region for optical probing of the content of the pores. Furthermore, the pores may be distributed over a desired length of the optical fiber so as to accumulate optical interaction between the probing light in the core and any analyte in the vials/cuvettes formed by the pores in order to achieve an enhanced signal-to-noise ratio.

By this particular configuration, it is achieved that a small, but representative analyte fraction is gently extracted from the complex fluid and efficiently exposed to the probing field with a high degree of overlap. This is achieved in a particularly simple and fast manner, since the pores are arranged transversely of the optical fiber with the openings at the circumferential surface, and with a relatively short distance from the opening to the location of probing, thus facilitating a particularly rapid diffusive exchange of the sample.

Typical cross-sectional dimensions of the pores are in the micron and sub-micron range down to about 100 nm. Analyte transport into and out of the pores is achieved by diffusion. For efficient operation, the pores are filled with a priming fluid, which preferably is filled into the pores in a priming step, e.g. prior to performing the first detection measurement. The priming fluid may not affect the fluid to be analyzed. The priming fluid thus has to be compatible with the fluid to be analyzed. Advantageously, the priming fluid may be a rinsing fluid, such as an aqueous buffer solution, which may also be used for rinsing a sample chamber during filling, emptying and re-filling procedures for replacing samples of a fluid to be analyzed. The rinsing fluid may also be a reference fluid or a calibration fluid.

Advantageously according to some embodiments, the pores are filled with a liquid. Priming the pores with a known liquid allows for extracting a subsample representative of the relevant components in the fluid to be analyzed into the pores by diffusion alone. This provides for a fast, efficient and well-controlled exchange of the analyte via the pores into and out of the optical probing region. Advantageously according to some embodiments, the liquid is an aqueous solution. This is particularly useful for the detection of water-soluble analytes. Alternatively, it is conceivable that the pores are filled with a non-aqueous liquid, which is particularly useful e.g. when the fluid to be analyzed is also a non-aqueous liquid.

The porous optical fiber is particularly useful for analyzing complex fluids comprising a continuous fraction and a discontinuous fraction, in particular for selectively detecting an analyte in the continuous fraction of the complex fluid. The fluid to be analyzed may contain at least a continuous fraction comprising the analyte. The fluid to be analyzed may further contain a discontinuous fraction, i.e. a particulate fraction. The particulate fraction may, for example, include solid particles, debris and other contaminants, biological cells (such as red blood cells) or microorganisms, liquid droplets, gas bubbles, and combinations thereof.

The fluid to be analyzed may be a whole blood sample, the plasma fraction of whole blood, spinal cord fluid, urine, pleura, ascites, wastewater, a pre-prepared fluid for any kind of injection, fluids with a constituent possible to detect by optical probing, such as spectroscopy, or a gas such as air, carbon dioxide containing gas, carbon monoxide containing gas.

The analyte may be any substance detectable by optical probing, such as a subset of molecules that may be present in the continuous phase of the fluid to be analyzed. For example, when analyzing a whole blood sample, the analyte may be a particular drug, and the measurement may be for determining a drug content in the plasma phase, e.g. to determine drug uptake and adjust dosing of the drug accordingly. In another example of analyzing a whole blood sample, the analyte may be bilirubin for determining a degree of hemolysis. In yet another example of analyzing a whole blood sample, the analyte may be carbon-dioxide.

The term "whole blood" refers to blood composed of blood plasma, and cellular components. The plasma represents about 50%-60% of the volume, and cellular components represent about 40%-50% of the volume. The cellular components are erythrocytes (red blood cells), leucocytes (white blood cells), and thrombocytes (platelets). Preferably, the term "whole blood" refers to whole blood of a human subject, but may also refer to whole blood of an animal. Erythrocytes constitute about 90%-99% of the total number of all blood cells. They are shaped as biconcave discs of about 7 μm in diameter with a thickness of about 2 μm in an un-deformed state. The erythrocytes are highly flexible, which allows them to pass through very narrow capillaries, reducing their diameter down to about 1.5 μm. One core component of erythrocytes is hemoglobin which binds oxygen for transport to the tissues, then releases oxygen and binds carbon dioxide to be delivered to the lungs as waste product. Hemoglobin is responsible for the red color of the erythrocytes and therefore of the blood in total. Leucocytes make up less than about 1% of the total number of all blood cells. They have a diameter of about 6 to about 20 μm. Leucocytes participate in the body's immune system e.g. against bacterial or viral invasion. Thrombocytes are the smallest blood cells with a length of about 2 to about 4 μm and a thickness of about 0.9 to about 1.3 μm. They are cell fragments that contain enzymes and other substances important to clotting. In particular, they form a temporary platelet plug that helps to seal breaks in blood vessels.

The terms "blood plasma" or "plasma" refer to the liquid part of the blood and lymphatic fluid, which makes up about half of the volume of blood (e.g. about 50%-60% by volume). Plasma is devoid of cells. It contains all coagulation factors, in particular fibrinogen and comprises about 90%-95% water, by volume. Plasma components include electrolytes, lipid metabolism substances, markers, e.g. for infections or tumors, enzymes, substrates, proteins and further molecular components.

The term "wastewater" refers to water that has been used, as for washing, flushing, or in a manufacturing process, and so contains waste products and/or particles and is thus not suitable for drinking and food preparation.

The terms "optical" and "light" and related terms generally refer to electromagnetic radiation in the visible, infrared, and ultraviolet spectral ranges: the term "visible" typically refers to electromagnetic radiation with wavelengths in the range of 400 nm-700 nm; the term "infrared" broadly refers to electromagnetic radiation with wavelengths in the range of 700 nm-1 mm, with typical subranges of about 700 nm-3 μm in the "near-infrared", 3 μm-50 μm in the "mid-infrared", and 50 μm-1 mm in the "far-infrared"; the term "ultraviolet" or "UV" broadly refers to electromagnetic radiation with wavelengths in the range of 10 nm-400 nm, with typical subranges of 300 nm-400 nm in the "near ultraviolet", 200 nm-300 nm in the "middle ultraviolet", and 122 nm-200 nm in the "far ultraviolet". The skilled person will understand that the usefulness of the mentioned spectral ranges for a given optical fiber, and in particular for a given core material, will depend on the compatibility of spectral ranges and materials for propagating input and output light through these materials.

Under operation, the circumferential surface of the porous optical fiber is contacted with a fluid to be analyzed, for example a whole blood sample. The small pores in the optical fiber communicate with the whole blood sample or fluid through the openings in the circumferential surface. The pore openings are dimensioned to selectively extract a sub-sample of the plasma phase of the whole blood sample, i.e. to extract a sub-sample of the fluid including the analyte. No red blood cells can enter the pores through the openings on the circumferential surface of the optical fiber. Nothing larger than the pore diameter can enter the pores which excludes e.g. any debris included in the fluid.

The sub-sample volume corresponds to the total internal volume of the pores. No filtration and net mass transport of any filtrate occurs through the pore containing layer during measurement—neither into any common filtrate recipient nor to any filtrate outlet. The optical detection is then performed only on the sub-sample contained in the pores. The confinement of the input light to the core of the optical fiber optically separates the optical probing region in an active section of the porous optical fiber from the fluid space containing the whole blood sample or the fluid. By optically separating the probing region from the fluid space, contributions of the intact red blood cells of the whole blood sample or of the debris in the fluid to the probed signal can be effectively suppressed. The measurement is thus specific to the content of analyte in the fluid.

The small sub-sample with a representative content of the relevant components may be transferred to the pores in any suitable manner. The small pores that are oriented essentially transverse of the optical fiber, leading directly into the core, allow for a very efficient and fast extraction of the sub-sample for optical probing from the fluid to be analyzed, such as a whole blood sample through the openings in the circumferential surface, by means of capillary forces and/or diffusion.

In a typical operation mode, the circumferential surface of the optical fiber is contacted by a rinsing fluid prior to contacting the circumferential surface with a whole blood sample or fluid that is to be analyzed. Thereby, the pores are 'primed' with a prefill of a liquid that is compatible with the whole blood sample or the fluid, and in particular a liquid that is compatible with the plasma phase if the fluid is whole blood, such as an aqueous solution commonly used for rinse, calibration and/or quality control purposes in blood analyzers. Typical rinse liquids used for e.g. wash-out in whole blood analyzer systems may be used as such a liquid. Rinse liquids are aqueous solutions comprising $K^+$, $Na^+$, $Cl^-$, $Ca^{2+}$, $O_2$, pH, $CO_2$, and $HCO_3^-$ in concentrations corresponding to human plasma. When the whole blood sample or fluid is then brought in contact with the circumferential surface that is primed with a compatible liquid, a representative subsample of components in the plasma phase of the whole blood sample or of the fluid is extracted and transferred in a very efficient and gentle manner by means of diffusion of the relevant components into the prefilled pore. In particular, any concentration gradient in the content of the analyte between the fluid and the reference liquid in the pores drives a diffusive transfer, thereby producing in the pores a sub-sample with an analyte concentration representative of the analyte concentration in the fluid.

In another operation mode, it may also be conceived to directly contact the circumferential surface of a dry sensor with a whole blood sample or a fluid sample. Further preferably in this operation mode, an inside surface of the pores is hydrophilic, thereby extracting the sub-sample from the whole blood sample or fluid sample at the circumferential surface of the optical fiber into the pores by means of capillary forces. When operating a porous optical fiber in this mode calibration could occur either via batch calibration as porous optical fibers produced in the same batch are expected to have equal sensitivity (e.g. equal light absorption when measuring on identical fluids). Alternatively, the pores of the optical fiber can contain a calibration dye with absorption characteristics different from the analyte. The calibration dye is useful for normalizing/calibrating the optical probing signal, while being spectrally distinguishable from the substance in a plasma sample, e.g. bilirubin, to be detected/measured. Since the calibration dye will not be present in the actual fluid to be analyzed, the calibration dye will diffuse out of the sensor during the measurement, meanwhile the analyte diffuses into the pores of the sensor. By optically probing the pores before and after acquiring the fluid, a quantitative measure for the substance to be detected (e.g. bilirubin) may be developed by a comparison of the calibration reference and fluid substance signals.

By providing the optical input through the core of the optical fiber itself, the content of the pores penetrating the core can conveniently be probed. Due to the confinement of the optical probing field to the core of the optical fiber, an optical probing region comprising the pores is optically separated from the fluid contacting the circumferential surface of the porous optical fiber. The optical probing is thus selectively performed only on the sub-sample inside the pores.

Light emerging from the pores in response to the illumination has interacted with the sub-sample in the pores and thus carries information on the sub-sample. The emerging light and/or a signal representative of the emerging light may then be analyzed with respect to that information in order to develop a value representative of the analyte content in the whole blood sample or in the fluid. Analysis may include spectrally analyzing the emerging/detected light, and/or signal/data processing, e.g. for comparing the obtained signal with signals obtained on calibration/reference samples, for noise filtering, for applying corrections, and for removing artefacts.

In a particularly advantageous embodiment for measuring hemolysis in whole blood samples, it is the coloring of the plasma by bilirubin that is probed optically, e.g. by using spectrally resolved absorbance measurements, or by measuring the spectrally integrated absorbance over a predetermined bandwidth within a spectral range indicative of the presence of bilirubin in the liquid sub-sample, such as within a spectral range of wavelengths 380 nm-750 nm, such as within a spectral range of wavelengths 400 nm-520 nm, or at about 455 nm.

Further according to some embodiments of the optical fiber, the pores are open ended pores. The term "open ended" refers to pores that continue all the way through the optical fiber. The pores are in fluid communication with the fluid space outwardly adjacent to the circumferential surface of the optical fiber, i.e. a sub-sample of the fluid to be analyzed is extracted for optical probing inside the pores and after the measurement discharged again through the same or the other opening of the pores in the circumferential surface.

Further according to some embodiments of the optical fiber, the pores are dead-end pores. The term "dead-end" refers to pores that end within the optical fiber. Dead-end pores do not continue all the way through the optical fiber or to any common reservoir or recipient inside the optical fiber. The pores are only in fluid communication with the fluid space outwardly adjacent to the circumferential surface of the optical fiber, i.e. a sub-sample of the fluid to be analyzed is extracted for optical probing inside the pores and after the measurement discharged again through the same openings in the circumferential surface.

Further according to some embodiments of the optical fiber, the pores are distributed in the longitudinal direction over an active section of length L.

Further according to some embodiments of the optical fiber, the pores are distributed in the end surface of the optical fiber. Hence, the active section is the end surface of the optical fiber and not in the longitudinal direction of the optical fiber.

In the section of the optical fiber where pores are formed, the optical fiber may be said to be 'active' or 'sensitive', since the pores are responsible for extracting and presenting the sub-sample inside the core for optical probing. The length L can e.g. be adapted to match geometric constraints of a sample chamber in which it is to be integrated so as to only provide an active section where the fluid sample can contact the circumferential surface of the optical fiber. The Length L of the active section may further be adapted to match e.g. a requirement of a minimum and/or maximum surface for contacting the fluid to be analyzed. Furthermore, for a given length L of the active section, the density of the pores may be adapted to match requirements of presenting a sufficiently large sample volume for optical probing. However, an excessive density of pores in the active section of the optical fiber may also be detrimental to a proper/sufficient confinement of the input optical field to the core of the optical fiber.

Advantageously according to some embodiments, the pores are "sparsely" distributed over the active length, i.e. balancing the requirement of providing a good overlap for the interaction between sample and the input optical field with the constraint not to affect or corrupt the light confining properties for propagating a stimulating input optical field through the entire sensitive/active region along the longitudinal direction of the optical fiber.

Further according to some embodiments of the optical fiber, the core has a diameter, wherein a depth of penetration of the pores into the core is at least 5%, or at least 10%, or at least 20%, or at least 40% of the diameter of the core. An increased penetration depth provides an increased overlap with the probing optical field. Diameter and penetration depth are measured in a radial direction, i.e. perpendicular to the longitudinal direction. The pores penetrate with a penetration depth d, as measured from the circumferential interface delimiting the core, in a radially inward direction, i.e. perpendicular to the longitudinal direction and towards the center of the core. Preferably, the pores penetrate "deeply" into the core material so as to provide a significant overlap between the mode power and the pore volumes acting as analyte vials/cuvettes.

Further according to some embodiments of the optical fiber, a cross-sectional dimension of the openings of the pores is about 1 µm or less, about 800 nm or less, preferably about 500 nm or less, or even about 400 nm or less. The cross-sectional dimension of the pore openings is preferably adapted so as to balance size selectivity (smaller pore opening diameter) against a rapid exchange of sub-sample/analyte (larger pore opening diameter)—depending on the application. The given values are, for example, particularly useful for the analysis of body fluids, such as whole blood with an analyte in the plasma fraction.

Further according to some embodiments of the optical fiber, a cross-sectional dimension of the openings of the pores is at least 200 nm. The cross-sectional dimension of the pore openings is preferably adapted so as to balance size selectivity (smaller pore opening diameter) against a rapid exchange of sub-sample/analyte (larger pore opening diameter)—depending on the application. The values of the recited range are, for example, particularly useful for the analysis of body fluids, such as whole blood with an analyte in the plasma fraction.

Further according to some embodiments of the optical fiber, a length of the pores in an axial direction along the pores is less than 100 µm, less than 50 µm, and preferably less than 30 µm. The length of the pores is preferably adapted so as to balance a desire to provide an increased sample volume (longer pore length) for interaction with the optical probing field in the core against rapid exchange of sample/analyte (shorter pore length)—depending on the application. The given values are particularly useful for the analysis of body fluids, such as whole blood with an analyte in the plasma fraction of the whole blood sample.

Further according to some embodiments of the optical fiber, a length of the pores in an axial direction along the pores is at least 1 µm, at least 2 µm, at least 5 µm, and preferably at least 10 µm. The length of the pores is preferably adapted so as to balance a desire to provide an increased sample volume (longer pore length) for interaction with the optical probing field in the core against rapid exchange of sample/analyte (shorter pore length)—depending on the application. The given values are particularly useful for the analysis of body fluids, such as whole blood with an analyte in the plasma fraction of the whole blood sample.

Further according to some embodiments of the optical fiber, the pores are straight. Straight-shaped pores facilitate an effective transport through the length of the pore, thereby achieving a fast sub-sample/analyte exchange.

Further according to some embodiments of the optical fiber, the pores are track-etched pores formed by exposing the optical fiber to a directional ion bombardment followed by chemical etching. Track-etching is particularly well-suited for forming straight-shaped and narrow, yet deep pores of e.g. the above-mentioned dimensions.

The pores may be formed in a unidirectional arrangement resulting, e.g. from a single directional ion bombardment exposure. Alternatively, the pores may be formed in a multi-directional arrangement by providing multiple directional ion bombardment exposures from different directions. Accordingly, a radial arrangement with pores extending essentially perpendicular to the circumferential surface may be conceived.

The pore arrangements may thus e.g. be created/defined by one or more directional ion-bombardment exposures prior to performing the etching steps.

Advantageously according to some embodiments of the optical fiber, a porosity of a given volume of the core material comprising pores is between 50% and 5% by volume, between 30% and 10% by volume, or about 15% by volume. The pores create porosity in the optical fiber (or in a given region of the optical fiber) with a corresponding surface area of the circumferential surface over which the openings of the pores are distributed. The porosity may be characterized in terms of the volume of the voids created in the core of the optical fiber by the pores, i.e. the pore volume penetrating into the core, wherein the pore volume is referred to the volume of the core of the optical fiber penetrated by the pores. This volume is here defined as the volume of a cylindrical shell between the circumferential interface area over which the pores are distributed with a thickness determined by the maximum depth of penetration of the pores into the core as seen in radial directions perpendicular to the circumferential interface delimiting the core.

In addition thereto, the porosity may be further characterized in terms of the integrated pore volume, which is equal to the sub-sample volume that is available for optical probing. The pore volume may conveniently be expressed as an equivalent pore volume depth DELTA, which is the pore volume referred to the corresponding circumferential surface area over which the pore openings are distributed, also referred to as active area. Accordingly, the porosity of the optical fiber can be converted into an equivalent pore volume depth DELTA as follows. The pores having an opening within a given active area A have a total pore volume V. The equivalent pore volume depth is then calculated as the total pore volume divided by the given active area: DELTA=V/A.

Advantageously according to some embodiments of the optical fiber, an equivalent pore volume depth DELTA is less than 20 µm, alternatively less than 10 µm, or preferably about 5 µm or less, wherein the equivalent pore volume depth DELTA is defined as the total volume of the pores V divided by an area A of the circumferential surface over which the openings of the pores are distributed. Thereby, a small sub-sample with a representative concentration of relevant components is obtained. A small subsample volume is desirable to promote a fast subsample exchange, thereby reducing response time of the sensor, and cycle time of measurements using the sensor. A small sub-sample volume is further desirable in order to avoid effects of depletion of boundary layers of the plasma fraction in the fluid sample, e.g. a whole blood sample, close to the circumferential surface of the optical fiber. Such depletion effect may otherwise occur in small, still standing samples, where particulate matter in the fluid, e.g. red blood cells, may obstruct an efficient diffusive exchange of relevant components from the volume of the fluid sample towards the boundary layer at the circumferential surface of the optical fiber, if the equivalent pore volume depth exceeds a critical value.

Preferably, an equivalent pore volume depth DELTA is at least 1 µm, alternatively at least 2 µm, or in the range from 3 µm to 5 µm, wherein the equivalent pore volume depth is defined as above. A larger sub-sample volume is desirable to achieve a better signal-to-noise level due to a larger sub-sample volume contributing to the optically probed information.

Further according to some embodiments, a useful compromise between reducing response time, reducing cycle time, and/or avoiding depletion effects in small still standing fluid samples, such as whole blood samples, on the one hand, and a required or desired signal-to-noise ratio on the other hand is found for an equivalent pore volume depth DELTA in the range from 1 µm to 20 µm, preferably in the range from 2 µm to 10 µm or at about 4 µm-5 µm.

Further according to some embodiments of the optical fiber, an inner wall surface of the pores is hydrophilic, e.g. coated with a hydrophilic coating. Thereby, an efficient capillary driven filling of dry pores with liquid is achieved. Furthermore, a hydrophilic coating prevents certain hydrophobic substances, such as hydrophobic dyes, hemoglobin, and other proteins, from depositing inside the pores that would otherwise lead to a gradual fouling of the sensor, which is difficult to wash out with an aqueous solution.

The optical fiber may comprise a hydrophilic coating of e.g. polyethylene glycol (PEG) to increase the diffusion into the pores. The hydrophilic coating may be chosen according to the use of the porous optical fiber. In some uses, the pores of the optical fiber will never dry out, once it is in use and it therefore only needs to be hydrophilic at startup for the purpose of efficient priming. For other uses of the porous optical fiber, the coating has to keeps it hydrophilicity permanently throughout a desired life time of the porous optical fiber, so as to allow the pores of the optical fiber to dry out and still be useable afterwards when the porous optical fiber is re-wetted for a further use.

Further according to some embodiments, the optical fiber is a polymer optical fiber, such as an optical fiber made of poly-methyl-methacrylate (PMMA), polyethylene terephthalate (PET or PETE), or an analogue of PET (polyethylene terephthalate polyester (PETP or PET-P)), or a polycarbonate (PC). These materials are well-suited for producing optical fibers. Furthermore, these materials have the advantage that they are particularly well suited for fabricating straight-shaped, narrow and deep pores, e.g. by means of track-etching.

Further according to some embodiments of the optical fiber, the optical fiber is a multimode optical fiber with a core supporting a plurality of modes propagating in the longitudinal direction. This allows for propagating and applying a broad spectral range of input light for probing the content of the pores penetrating the core. Furthermore a multimode fiber has typically a larger diameter core and therefore may be configured mechanically more stable and rugged as compared to a single mode optical fiber with a typical core diameter of below 10 µm. This is particularly relevant for configurations where outer layers of the optical fiber in the active section of the porous optical fiber are thinned down, partially removed, or completely stripped, ultimately leaving only the core material for contacting the fluid to be analyzed.

Further according to some embodiments of the optical fiber, the core has a diameter in the range between 5 µm and 500 µm, preferably between 100 µm and 200 µm. Multimode optical fibers with a core diameter in this range provide a good candidate for efficient injection of optical probing power over a broad spectral range, which is rugged to allow for easily stripping the optical fiber down to the core material, and for providing adequately narrow and deep pores in the core material.

Further according to some embodiments of the optical fiber, the circumferential interface of the core forms the circumferential surface. This "stripped core" configuration provides direct access from the openings of the pore into the core where the probing light is confined, thereby allowing for a particularly efficient and fast sample exchange.

Further according to some embodiments, the optical fiber further comprises a reflective coating on the circumferential surface. The reflective coating is thus arranged between the core material and the fluid to be analyzed so as to cover the circumferential surface apart from the openings giving access to the pores. The reflective layer is adapted to reflect light reaching the reflective layer from the inside of the optical fiber, thereby preventing probing light from reaching and interacting with the fluid at the outside of the optical fiber. Thereby, the spatial selectivity for optical probing only inside the pores may be further enhanced as compared to a porous optical fiber configuration without reflective layer. A reflective layer may be particularly useful for porous optical fibers where any outer layers have been removed, leaving only the stripped core in the active section comprising the pores. Thereby an improved confinement of the optical probing field to the core may be achieved, in particular in the active section.

Advantageously according to one embodiment the reflective layer is made of metal. Such metallic coatings can be applied in a relatively cost-effective, yet well-controlled manner with adequate reflectivity.

Advantageously according to one embodiment the reflective layer is made of platinum, palladium or an alloy comprising as a principal component platinum or palladium. These materials exhibit a good reflectivity in the spectral range of the electromagnetic spectrum (deep violet to blue) that is relevant for the detection of certain substances, e.g. free hemoglobin, for example by absorbance probing. Furthermore, these materials are biocompatible and do not e.g. introduce artificial hemolysis. Furthermore, these materials are chemically stable in general and in particular in the chemical environment of biological fluids, such as a whole blood sample or any of the previously mentioned body fluids.

Alternatively, according to some embodiments, the reflective layer may be made of silver or aluminum. Further advantageously according to some embodiments, the surfaces of the reflective layer facing towards the sample volume are encapsulated by an additional passivation layer, thereby enhancing the lifetime of the device, in particular when using silver or aluminum as a material for the reflective layer. A suitable passivation may be made of e.g. a thin layer of $SiO_2$ which preferably is made transparent and has to be sufficiently thin so as to not obstruct the opening of the pores. These materials may also provide a good reflectivity in the relevant spectral range (red), are biocompatible and chemically stable in the environment.

Advantageously according to one embodiment, the thickness of the reflective layer is between 10 nm-100 nm depending upon the used metal. Such a layer thickness allows for applying the reflective layer by an evaporation technique without clogging of the openings of the pores at the circumferential surface of the optical fiber. At the same time, the layer thickness has to be sufficient to provide adequate attenuation of light propagating to the sample volume in order to ensure an enhanced optical separation between the probing region and the sample volume containing the fluid to be analyzed, e.g. a whole blood sample. Preferably, the transmitted light is less than 5%, less than 1% or even less than 0.1% in the spectral range of detection, i.e. in the spectral range from which a signal representative of the relevant component is developed. For example, for measuring bilirubin in the plasma fraction of a whole blood sample suitable spectral ranges are from 380 nm to 700 nm, from 380 nm to 450 nm, or at about 416 nm.

Further according to some embodiments of the optical fiber, the circumferential interface of the core is for contacting the fluid to be analyzed. The circumferential interface of the core material may be configured to be directly exposed to the fluid to be analyzed. Such a configuration may be easier to produce, and may e.g. be applicable, where confinement requirements for the optical probing field is not as stringent. Furthermore, such a configuration may be useful when using an off-axis detection arrangement.

A second aspect of the invention relates to a sensor system for the detection of an analyte in a fluid by optical probing, the sensor comprising a porous optical fiber according to any one of the herein disclosed embodiments; a light source coupled to the first end for injecting input light into the optical fiber; and a detector arranged to receive output light emitted from the pores in response to illumination by the injected input light.

The sensor system is advantageous in that it is easy to integrate with a sample chamber in which a sample of the fluid to be analyzed is prepared and brought in contact with the active region of the porous optical fiber. The sensor system is further particularly well suited for integration in a system with a re-usable sample chamber that can be loaded with a sample, rinsed after sample discharge and prepared for analysis of a new sample independent of the first sample. Due to the good adaptability for easy integration with an analysis system, the porous optical fiber based sensor is also particularly well suited for integration with a multiple parameter analyzer for the analysis with respect to a plurality of measurable parameters performed on the same sample, in particular in systems using only small sample volumes at a time.

Optical probing light may be performed by any suitable optical probing arrangement. Input light may be injected into the optical fiber at one end, for propagation along the longitudinal direction of the optical fiber confined to the core until the light encounters the pores containing a representative sub-sample of the fluid to be analyzed by optical probing with respect to one or more analytes. The illuminating input light interacts with the sub-sample and the light emitted from the sub-sample in response to the illumination is collected by a detector. As discussed before, by presenting the sub-sample in pores penetrating deeply into the core where the input light is confined, a particularly good overlap, and thus interaction of the optical probing field with the sample to be analyzed is achieved. As a consequence, a good sensitivity of the optical analyte response can be achieved by the sensor system with the porous optical fiber. The optical arrangement may include further optical elements improving coupling of the probing light into the optical fiber and improving coupling of the light emerging from the optical fiber into the detector input.

The light source may in principle be any light source that transmits light in a region where the analyte in the pores absorbs light or otherwise provides an optically stimulated response in order for the system to work. When light sources age, they might change characteristic, e.g. emit less light or drift may affect the peak amplitude. This may be compensated by using a feedback calibration process, where the detector measures the light received through the porous optical fiber in a situation where the pores in the porous optical fiber are expected to be clean, i.e. contain no molecules in the pores absorbing light. If the amplitude of the light received is smaller than expected, the feedback loop to the light source may control that the current or voltage to the light source is increased, to compensate for the degradation of the light source. Alternatively, if the light source has changed characteristics, the calculation of the actual absorption when measuring may adjust for this change of the emitted light compared to the original factory calibration.

Advantageously according to one embodiment the detector includes a spectrophotometer and an optical probing device is configured for the spectrophotometric analysis of the light emerging from the probing region in the optical fiber. This allows for resolving the spectral signature of one or more relevant components in the light emerging from the sub-sample in the probing region. The detector may be a photodiode or a spectrometer that is able to detect the absorption over a given spectral range. Alternatively, an array or diodes may be used, where each diode emits light at different wavelengths, and a photodiode is used as a detector. The diodes may be multiplexed to emit light in different intervals. The absorption is then found by comparing the lights emitted from a diode in that particular interval compared with the light detected by the photodiode.

The porous fiber can be used as a reading device for color producing/consuming assays. The advantage being that it is not necessary to perform separation steps in order to produce plasma before the assay. By way of example, the following types of assays may be used with the porous optical fiber based sensor system: Sandwich assays, where the receptor ligand could be bound inside the membrane channels; Assays where one part is bound in the pores, e.g. Bromocresol Green Albumin assay, which use bromocresol green, to form a colored complex specifically with albumin. The intensity of the color, measured at 620 nm, is directly proportional to the albumin concentration in the fluid; Enzyme activity assays as e.g. the aspartate aminotransferase (AST) activity assay kit, where the transfer of an amino group from aspartate to α-ketoglutarate results in the generation of glutamate, resulting in the production of a colorimetric (450 nm) product proportional to the AST enzymatic activity present.

The porous optical fiber based sensor system could also be used in non-medical applications such as monitoring tasks for beer brewing, wastewater analysis, food testing and in dye production. In beer brewing a precise color is desired. The porous optical fiber based sensor system could be used to determine whether or not the beer has the desired color or not by measuring on the liquid and compare the reading with a liquid of correct color. Wastewater could be analyzed for presence or absence of a constituent. In food testing, liquids such as milk, juices and other slurries, the porous optical fiber based sensor system could be used for analysis for presence or absence of a constituent or analyte. Other chemical reactors e.g. the dye industry could be using the porous optical fiber based sensor system to obtain the desired color, content or other chemical properties for their liquids.

Advantageously according to some embodiments, the porous optical fiber based sensor system, or a blood analysis system comprising a porous optical fiber based sensor system, further comprises a processor configured for comparing the signal generated by the detector with a predetermined calibration reference to develop a quantitative measure of the analyte level in the fluid.

Further advantageously according to some embodiments, the calibration reference is obtained on a dye-based calibration solution, such as an aqueous solution comprising tartrazine dye. Preferably, the dye-based aqueous solution is prepared from a typical rinse liquid with the addition of the calibration dye, such as tartrazine.

According to a further aspect of the invention a system for analyzing a fluid comprises (a) a fluid chamber with inlet and outlet ports for feeding and discharging the fluid; (b) a first detector adapted to provide a first signal representative of a level of an analyte in the fluid. Advantageously according to some embodiments, the system for analyzing a fluid further comprises (c) one or more further detectors, each further detector being adapted to provide a respective further signal representative of an analyte of the fluid; wherein the first and further detectors are operable to obtain the first and the one or more further signals from the same fluid, wherein the first detector is configured as a porous optical fiber for the optical detection of an analyte according to any of the embodiments disclosed herein.

Further according to some embodiments of the sensor system, the detector is arranged in-line in a forward scattering configuration at the second end of the optical fiber. This configuration is adapted to collect light propagated in a forward direction along the core from the second end of the optical fiber opposite to the first end where the input light is injected.

Further according to some embodiments of the sensor system, the detector is arranged in-line in a back-scattering configuration at the first end of the optical fiber.

This configuration is adapted to collect light propagated in a backward direction along the core from the first end of the optical fiber, i.e. the optical probing response is collected from the same end where the input light is injected.

Further according to some embodiments of the sensor system, the detector is arranged off-axis in an outward scattering configuration. The term off-axis refers to a direction having a finite angle with the longitudinal direction of the optical fiber. This configuration is adapted to collect light scattered out of the confinement by the optical fiber, i.e. the optical response is collected from directions that are off-axis with respect to the propagation of the input light that is confined to the core of the optical fiber.

Further according to some embodiments, the sensor system further comprises a sample chamber for receiving a fluid sample to be analyzed, the sample chamber enclosing the active section of the porous optical fiber.

According to a yet further aspect of the invention, a method of optically detecting an analyte such as bilirubin in a fluid is provided as detailed in the following. The method at least achieves the same advantages as discussed above with respect to respective embodiments of a porous optical fiber for detecting an analyte, or of a sensor system comprising such a porous optical fiber.

According to some embodiments, a method of optically detecting an analyte in a fluid comprises the steps of providing a porous optical fiber as disclosed above; contacting the porous optical fiber with a reference liquid so as to fill the pores with the reference liquid; contacting the circumferential surface of the porous optical fiber with a fluid; waiting for a diffusion time to allow for diffusion of the analyte in the fluid into the pores to stabilize; injecting input light into the core of the optical fiber; propagating the input light along the core to interact with the pores in the active section of the porous optical fiber; collecting light emitted from the pores in response to the input light, thereby optically probing the fluid inside the pores; and, based on the result of the optical probing, establishing an analyte level of the fluid. Preferably, the reference liquid is an aqueous solution that is compatible with the fluid, and in particular with the fraction thereof that may enter the pores, such as a liquid for rinse, calibration and/or quality control. In some embodiments, it may be conceived to omit the step of contacting the circumferential surface of the optical fiber with a reference liquid prior to introducing the fluid. However, including the step allows for a purely diffusive sub-sample extraction, which is very efficient and leads to a surprisingly fast detection response and surprisingly short cycle time for the measurement. Most advantageously, an analyte is detected optically in the pores by the color change due to the presence of the analyte in representative amounts in the extracted sub-sample.

Advantageously according to some embodiments, optical probing comprises performing a spectrophotometric analysis of the light emerging from the pores as an optical response to the probing input light.

Advantageously according to some embodiments, optical probing is measuring the absorbance. This has the advantage of a relatively simple, yet effective set-up.

Advantageously according to some embodiments the method further comprises the step of comparing the optical response with a predetermined calibration reference. Thereby, a quantitative measure of the analyte level in the fluid may be developed.

Further advantageously according to some embodiments of the method, the calibration reference is obtained on a dye-based calibration solution, such as an aqueous solution comprising tartrazine dye. Preferably, the dye-based aqueous solution is prepared from a typical rinse liquid with the addition of the calibrant dye, such as tartrazine.

BRIEF DESCRIPTION OF THE DRAWINGS

Preferred embodiments of the invention will be described in more detail in connection with the appended drawings, which show schematically in FIG. 1 an optical fiber with a porous section according to a first embodiment.

DETAILED DESCRIPTION OF PREFERRED EMBODIMENTS

Figure 1:
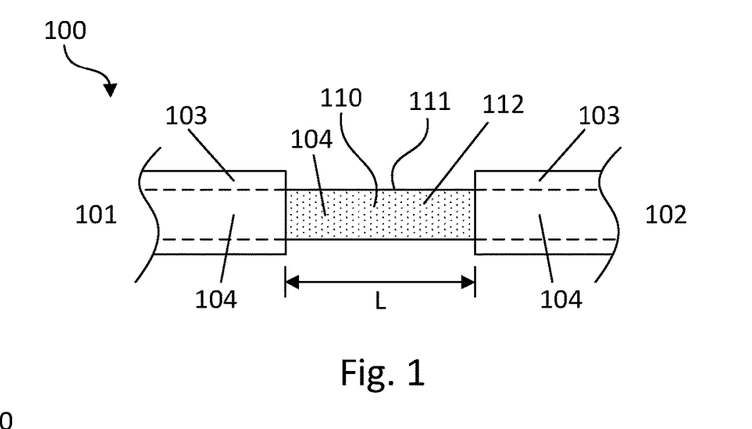

FIG. 1 shows an optical fiber 100 with a first end 101 and a second end 102 opposite to the first end 101 as seen in a longitudinal direction of the optical fiber 100. The optical fiber 100 is adapted for propagating light there through, confined to a core 104, along the longitudinal direction. At an intermediate location, the optical fiber 100 comprises an active section 110 of length L, where outer layers of the optical fiber, such as a cladding layer 103 are removed or thinned down to reveal a circumferential surface 111 from which pores 112 penetrate into the core material 104, thus allowing any substance present inside the pores 112 to interact with probing light propagated in the core 104 and to provide a corresponding optical probing response.

Figure 2:
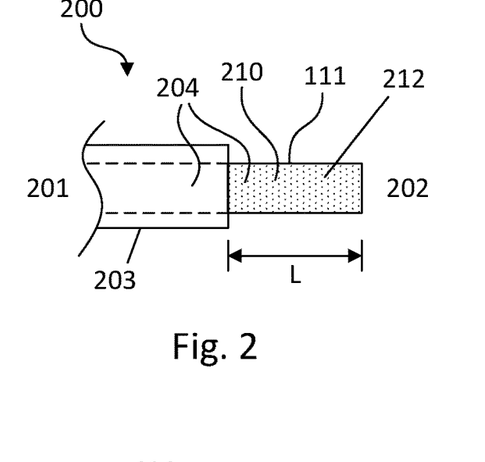
FIG. 2 an optical fiber with a porous section according to a second embodiment.

FIG. 2 shows an optical fiber 200 with a first end 201 and a second end 202 opposite to the first end 201 as seen in a longitudinal direction of the optical fiber 200. The optical fiber 200 is adapted for propagating light there through, confined to a core 204, along the longitudinal direction. The optical fiber 200 also comprises an active section 210 of length L, where outer layers of the optical fiber 200, such as a cladding layer 203 are removed or thinned down to reveal a circumferential surface 211 from which pores 212 penetrate into the core material 204, thus allowing any substance present inside the pores 212 to interact with probing light propagated in the core 204 and to provide a corresponding optical probing response. In contrast to the embodiment shown in FIG. 1, the active section 210 of the optical fiber 200 is located at an end location, namely at the second end 202.

Referring to FIGS. 3-6, different configurations of pore arrangements in the active section of a porous optical fiber are now schematically illustrated. FIGS. 3-6 show end projections of the active section of an optical fiber, such as those shown in FIGS. 1 and 2, as seen along the longitudinal direction of the optical fiber. The projection view shows pores from different longitudinal locations in superposition, i.e. the different pores shown in the figures are typically not located in the same cross-sectional plane. On the contrary, the pores are typically distributed over a certain lengthwise portion of the active section (i.e. over a certain depth in the projection view of FIGS. 3-6). The pores are preferably straight-shaped, and may e.g. be formed by track-etching as described above.

Figure 3:
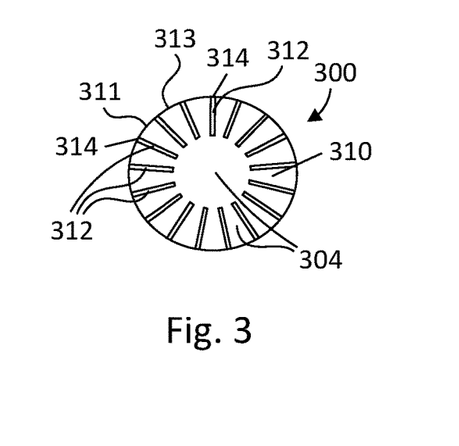
FIGS. 3-6 end projections of the porous section as seen along the longitudinal direction of the optical fiber according to different embodiments.

In particular, FIG. 3 shows an end projection view of an active section 310 of an optical fiber 300 where the outer layers have been stripped away leaving only the core material 304. A circumferential surface 311 of the active region 310 is formed by and coincides with the circumferential interface 313 delimiting the core 304 in radial directions perpendicular to the longitudinal direction. Pores 312 project radially inward from respective openings 314 at the circumferential surface 311 to a penetration depth equal to the length of the pores, about 30% of the diameter of the core 304 from each side. While the pores 312 are shown to be equally spaced and distributed in a circumferential direction, it should be noted that the pores may equivalently be distributed with a random spacing.

Figure 4:
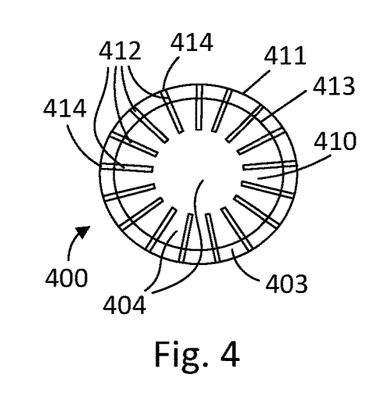
Figure 5:
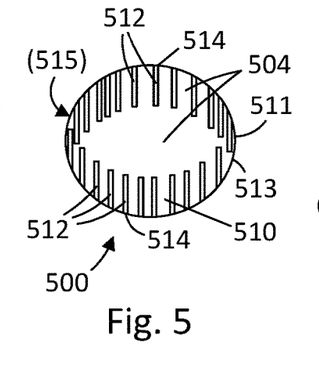

FIG. 4 shows an end projection view of an active section 410 of an optical fiber 400 with pores 412 in a radial arrangement corresponding to that of the embodiment shown in FIG. 3. However, the embodiment of FIG. 4 differs from the embodiment of FIG. 3 in that a cladding layer 403 remains around the core 404. The outer cladding layer 403 has circumferential surface 411 and is separated from the core 404 by circumferential interface 413. The pores 412 extend from openings 414 at the circumferential surface, through the cladding layer 403, and penetrate through the circumferential interface 413 deeply into the core 404. While the cladding layer 403 may evanescently carry some power of the optical field confined to and propagating along the core 404, in configurations with remaining outer layers surrounding the core 404 as shown here in FIG. 4, the pores 412 importantly penetrate into the core 404 in order to provide a significant spatial overlap for the optical probing of the content of the pores 412.

FIG. 5 shows again an end projection view of an active section 510 of an optical fiber 500 where the outer layers have been stripped away leaving only the core material 504. A circumferential surface 511 of the active region 510 is formed by and coincides with the circumferential interface 513 delimiting the core 504 in radial directions perpendicular to the longitudinal direction. Pores 512 extend from openings 514 at the circumferential surface into the core 504. In contrast to the embodiments of FIGS. 3 and 4, the pores 512 of the porous optical fiber 500 are straight-shaped and arranged essentially parallel to each other, penetrating into the material of the core 504 from two opposite directions. Such a configuration may conveniently obtained using a track-etching process by exposing the stripped section 510 of the optical fiber 500 to a unidirectional ion bombardment from two different directions (here two opposite directions) transverse of the longitudinal direction, and subsequently applying an etching step adapted to selectively remove material along the tracks of the ion-bombardment in the material of the optical fiber.

Figure 6:
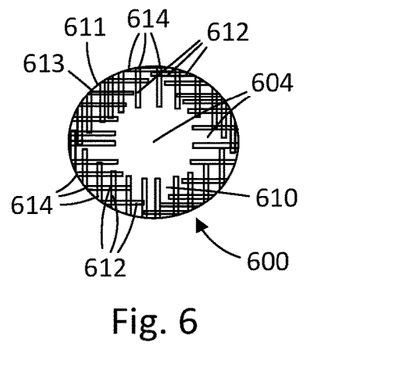

FIG. 6 also shows an end projection view of an active section 610 of an optical fiber 600 where the outer layers have been stripped away leaving only the core material 604. A circumferential surface 611 of the active region 610 is formed by and coincides with the circumferential interface 613 delimiting the core 604 in radial directions perpendicular to the longitudinal direction. Pores 612 extend from openings 614 at the circumferential surface into the core 604. The arrangement of the pores 612 in the embodiment of FIG. 6 corresponds to the arrangement of the pores 512 in the embodiment of FIG. 5 with the difference that the pores are not only formed from two opposite directions, but from four different transverse directions at about 90 degrees of each other. In fact, any combination of different directions and angles may be conceived in order to obtain a desired arrangement of pores similar to those of FIGS. 5 and 6.

Figure 7:
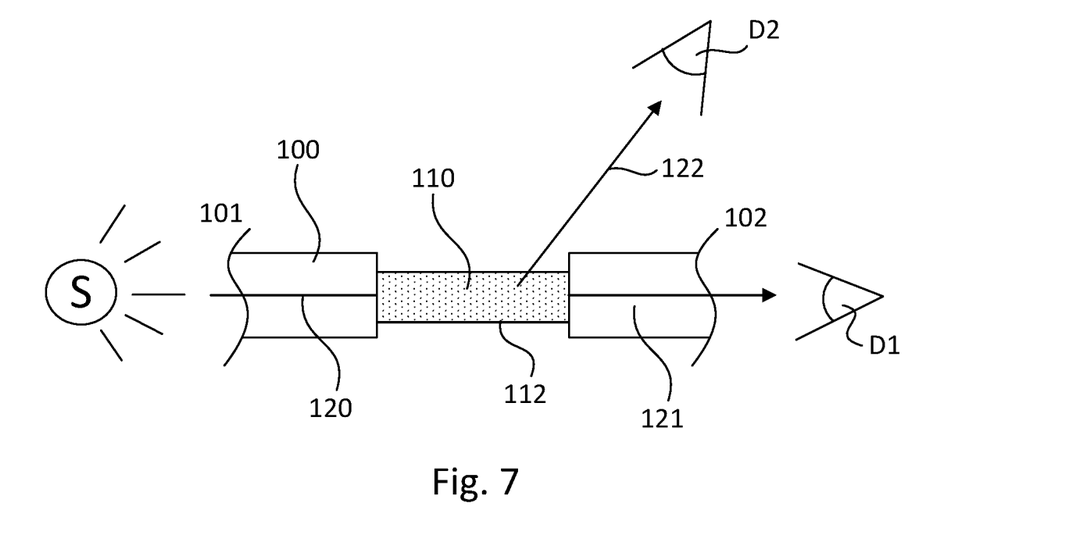
FIG. 7 a sensor with a porous optical fiber and an optical probing arrangement in two different detection configurations.
Figure 8:
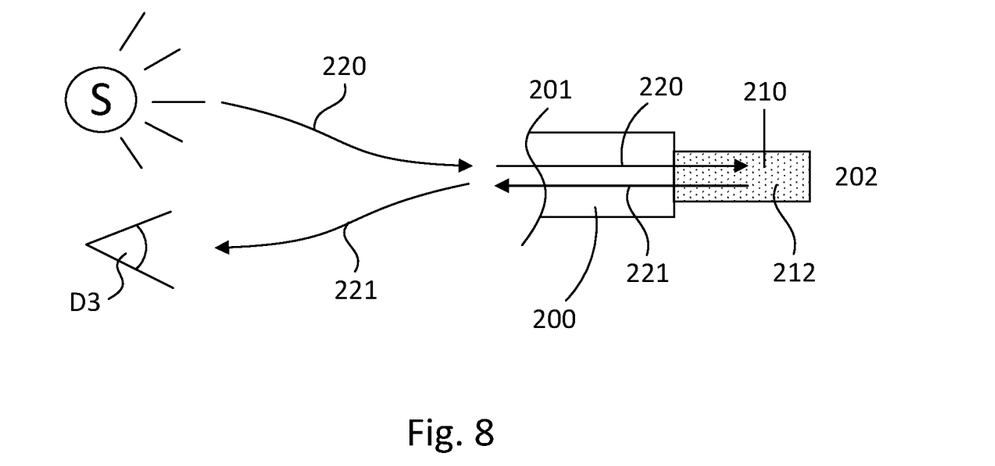
FIG. 8 a sensor with a porous optical fiber and an optical probing arrangement using a yet further detection configuration.
Figure 9:
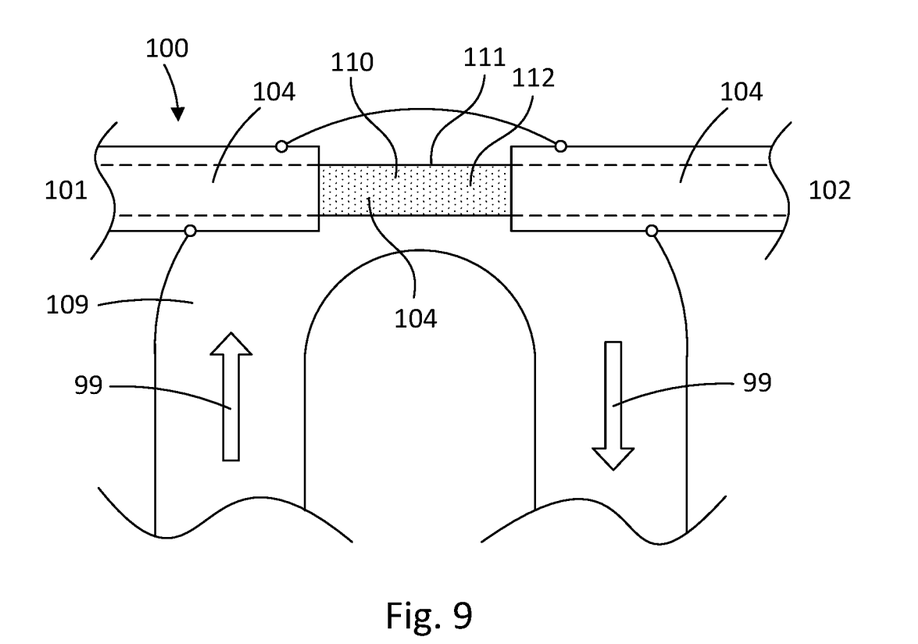
FIG. 9 a porous optical fiber integrated in a sample chamber according to one embodiment; and in FIG. 10 a porous optical fiber integrated in a sample chamber according to another embodiment.
Figure 10:
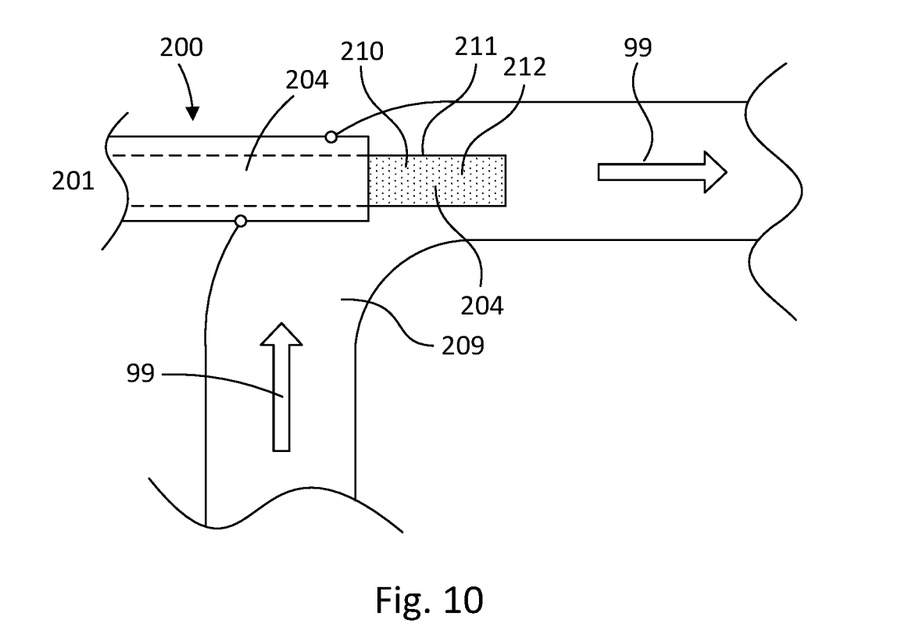

Turning now to FIGS. 7-10 different sensor systems are briefly explained by way of example, wherein FIGS. 7 and 8 schematically illustrate different optical probing configurations, and wherein FIGS. 9 and 10 illustrate different arrangements for the integration of a porous optical fiber with a sample chamber.

FIG. 7 shows an optical fiber 100 as the one shown above in FIG. 1. Optical fiber 100 has an active section 110 at an intermediate longitudinal location between a first end 101 and a second end 102. A light source S is coupled to the first end 101 of the optical fiber 100 to inject input probing light 120, which is propagated along the core of the optical fiber to the active section 110 with pores 112 containing a subsample of a fluid to be probed. The input probing illumination 120 causes an optical response carrying information on the content of the pores, which may be collected as forward probing response 121 by means of a detector D1 arranged in-line with the optical fiber in a forward scattering arrangement at the second end 102. Alternatively or in addition thereto, an off-axis probing response 122 may be collected by means of a detector D2 arranged off-axis with respect to the longitudinal direction of the optical fiber 100 in an outward scattering arrangement.

FIG. 8 shows an optical fiber 200 as the one shown above in FIG. 2. Optical fiber 200 has an active section 210 at an end-location at a second end 202 opposite to the first end 201. A light source S is coupled to the first end 201 of the optical fiber 200 to inject input probing light 220, which is propagated along the core of the optical fiber to the active section 210 with pores 212 containing a subsample of a fluid to be probed. The input probing illumination 220 causes optical response carrying information on the content of the pores. The optical response may be collected as backward probing response 221 by means of a detector D3 at the first end 201 in-line with the optical fiber 200 in a backward scattering arrangement. It may be noted that the different scattering configurations for optical probing may be combined according to the desired optical probing design. For example, the backward scattering configuration discussed here may be equally useful in combination with an optical fiber 100 as shown above in FIGS. 1 and 7.

FIG. 9 shows the integration of a sensor system having a porous optical fiber 100 as the one discussed above in a sample chamber 109 for contacting the active section 110 with a fluid sample 99, wherein the associated optical probing arrangement has been omitted for reasons of clarity. The sample chamber 109 may be of the "feed, fill, and empty" type where a fluid sample 99 is fed through an inlet to fill the sample chamber with the fluid 99 to be analyzed, and where, after measurements have been completed, the sample chamber is emptied through an outlet (and rinsed) to prepare the sample chamber for re-use. Alternatively, the sample chamber may be of the flow-through type, where a fluid sample 99 is continuously flown through the sample chamber 109 (e.g. formed as a channel as indicated in FIG. 9), thereby exposing the active section 110 of the optical fiber 100 to the fluid 99 to be analyzed. In either case, the circumferential surface 111 of the active section 110 is contacted by the fluid sample 99, whereby a sub-sample is extracted into the pores 112 and presented for optical probing in the core 104 of the optical fiber 100.

Likewise, FIG. 10 shows the integration of a sensor system having a porous optical fiber 200 as the one discussed above in a sample chamber 209 for contacting the active section 210 with a fluid sample 99, wherein the associated optical probing arrangement has been omitted for reasons of clarity. The sample chamber 209 may be of the "feed, fill, and empty" type where a fluid sample 99 is fed through an inlet to fill the sample chamber with the fluid 99 to be analyzed, and where, after measurements have been completed, the sample chamber is emptied through an outlet (and rinsed) to prepare the sample chamber for re-use. Alternatively, the sample chamber may be of the flow-through type, where a fluid sample 99 is continuously flown through the sample chamber 209 (e.g. formed as a channel as indicated in FIG. 10), thereby exposing the active section 210 of the optical fiber 200 to the fluid 99 to be analyzed. In either case, the circumferential surface 211 of the active section 210 is contacted by the fluid sample 99, whereby a sub-sample is extracted into the pores 212 and presented for optical probing in the core 204 of the optical fiber 200.

The invention is not limited to the above-mentioned embodiments and the skilled person may combine different features of the shown embodiments without leaving the scope of the present invention. For example, an optional reflective coating, such as a metallic coating may be applied to the circumferential surface of the active section of the porous optical fiber, such as indicated by reference numeral 515 in FIG. 5.

The invention claimed is:

1. A porous optical fiber for the detection of an analyte in a fluid by optical probing, the optical fiber having a first end and a second end opposite to the first end, as seen in a longitudinal direction, and a circumferential surface delimiting the optical fiber in radial directions perpendicular to the longitudinal direction,
   the optical fiber comprising:
      a core supporting at least one optical mode propagating in the longitudinal direction, the core having a circumferential interface delimiting the core in the radial directions;
      pores penetrating from an opening at the circumferential surface through the circumferential interface into the core of the optical fiber, wherein a cross-sectional dimension of the openings is dimensioned so as to prevent a particulate fraction of the fluid from entering the pores, while allowing the analyte to enter the pores; and
      a reflective coating on the circumferential surface.

2. The optical fiber according to claim 1, wherein the pores are dead-end pores.

3. The optical fiber according to claim 1, wherein the pores are distributed in the longitudinal direction over an active section of length L.

4. The optical fiber according to claim 1, wherein the core has a diameter, wherein a depth of penetration of the pores into the core is at least 5% of the diameter of the core.

5. The optical fiber according to claim 1, wherein a cross-sectional dimension of the openings of the pores is about 1 μm or less.

6. The optical fiber according to claim 1, wherein a cross-sectional dimension of the openings of the pores is at least 200 nm.

7. The optical fiber according to claim 1, wherein a length of the pores in an axial direction along the pores is less than 100 μm.

8. The optical fiber according to claim 1, wherein a length of the pores in an axial direction along the pores is at least 1 μm.

9. The optical fiber according to claim 1, wherein the pores are straight.

10. The optical fiber according to claim 1, wherein the pores are track-etched pores formed by exposing the optical fiber to a directional ion bombardment followed by chemical etching.

11. The optical fiber according to claim 1, wherein an inner wall surface of the pores is coated with a hydrophilic coating.

12. The optical fiber according to claim 1, wherein the optical fiber is a polymer optical fiber.

13. The optical fiber according to claim 1, wherein the optical fiber is a multimode optical fiber with a core supporting a plurality of modes propagating in the longitudinal direction.

14. The optical fiber according to claim 1, wherein the core has a diameter in the range between 5 μm and 500 μm.

15. The optical fiber according to claim 1, wherein the circumferential interface of the core forms the circumferential surface.

16. The optical fiber according to claim 1, wherein the circumferential interface of the core is for contacting the fluid to be analyzed.

17. A sensor system for the detection of an analyte in a fluid by optical probing, the sensor comprising a porous optical fiber according to claim 1; a light source coupled to the first end for injecting input light into the optical fiber; and a detector arranged to receive output light emitted from the pores in response to illumination by the injected input light.

18. The system according to claim 17, wherein the detector is arranged in-line in a forward scattering configuration at the second end of the optical fiber.

19. The system according to claim 17, wherein the detector is arranged in-line in a back-scattering configuration at the first end of the optical fiber.

20. The system according to claim 17, wherein the detector is arranged off-axis in an outward scattering configuration.

21. The system according to claim 17, further comprising a sample chamber for receiving a fluid sample to be analyzed, the sample chamber enclosing the active section of the porous optical fiber.

* * * * *